(12) United States Patent
Nguyen et al.

(10) Patent No.: US 9,186,314 B2
(45) Date of Patent: *Nov. 17, 2015

(54) COMPOSITIONS AND METHODS FOR SEALING THE SURFACE OF KERATINOUS SUBSTRATES

(71) Applicant: L'OREAL, Paris (FR)

(72) Inventors: Nghi Van Nguyen, Edison, NJ (US);
Sawa Hashimoto, Garwood, NJ (US);
Siliu Tan, Westfield, NJ (US)

(73) Assignee: L'OREAL (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/762,707

(22) Filed: Feb. 8, 2013

(65) Prior Publication Data

US 2013/0149274 A1    Jun. 13, 2013

Related U.S. Application Data

(63) Continuation-in-part of application No. PCT/US2011/046999, filed on Aug. 9, 2011.

(60) Provisional application No. 61/371,992, filed on Aug. 9, 2010, provisional application No. 61/372,006, filed on Aug. 9, 2010, provisional application No. 61/371,997, filed on Aug. 9, 2010, provisional application No. 61/371,983, filed on Aug. 9, 2010.

(51) Int. Cl.
| *A61K 8/86* | (2006.01) |
| *A61K 8/42* | (2006.01) |
| *A61Q 5/00* | (2006.01) |
| *A61Q 19/00* | (2006.01) |
| *A61K 8/41* | (2006.01) |
| *A61Q 5/02* | (2006.01) |
| *A61Q 5/12* | (2006.01) |
| *A61Q 17/04* | (2006.01) |
| *A61K 8/81* | (2006.01) |
| *A61Q 19/08* | (2006.01) |

(52) U.S. Cl.
CPC ... *A61K 8/86* (2013.01); *A61K 8/42* (2013.01); *A61Q 5/004* (2013.01); *A61Q 19/00* (2013.01); *A61K 8/41* (2013.01); *A61K 8/8158* (2013.01); *A61Q 5/02* (2013.01); *A61Q 5/12* (2013.01); *A61Q 17/04* (2013.01); *A61Q 19/08* (2013.01)

(58) Field of Classification Search
CPC ........... A61K 8/41; A61K 8/86; A61Q 5/004; A61Q 17/04
USPC ................................ 424/70.13, 70.16, 70.11
See application file for complete search history.

(56) References Cited

U.S. PATENT DOCUMENTS

| 6,432,390 | B1 * | 8/2002 | Fishman et al. ................ 424/60 |
| 6,660,045 | B1 | 12/2003 | Hoeffkes et al. |
| 2002/0155962 | A1 | 10/2002 | Cincotta et al. |
| 2009/0053161 | A1 | 2/2009 | Nguyen et al. |
| 2009/0071495 | A1 | 3/2009 | Nguyen et al. |

OTHER PUBLICATIONS

Merriam-Webster, definition of polyacid; downloaded from http://www.merriam-webster.com/medical/polyacid Sep. 9, 2014.*
International Search Report for Application No. PCT/US2011/046999 dated Mar. 23, 2012.
International Preliminary Report on Patentability for Application No. PCT/US2011/046999 dated Feb. 12, 2013.

* cited by examiner

*Primary Examiner* — Johann R Richter
*Assistant Examiner* — Yanzhi Zhang
(74) *Attorney, Agent, or Firm* — Lerner, David, Littenberg, Krumholz & Mentlik, LLP

(57) ABSTRACT

The present disclosure relates to a composition comprising: (a) at least one polyacid; (b) at least one amino compound chosen from alkyl monoamines, alkoxylated polyamines, alkoxylated monoamines, polyamines and mixtures thereof; and (c) cosmetically acceptable carrier. The present disclosure also relates to a method of sealing the surface of a keratinous substrate using such compositions, including inhibiting loss of hair color. The compositions of the present disclosure may further comprise an auxiliary ingredient.

17 Claims, No Drawings

COMPOSITIONS AND METHODS FOR SEALING THE SURFACE OF KERATINOUS SUBSTRATES

CROSS-REFERENCE TO RELATED APPLICATION

The present application is a continuation in part of International Application No. PCT/US2011/046999 filed 9 Aug. 2011, which claims the benefit of the filing date of U.S. Provisional Applications No. 61/371,983 filed 9 Aug. 2010, No. 61/371,992 filed 9 Aug. 2010, No. 61/371,997 filed 9 Aug. 2010, and No. 61/372,006 filed 9 Aug. 2010, all of which are incorporated herein by reference.

TECHNICAL FIELD

The disclosure relates to compositions and methods for sealing the surface of keratinous substrates in order to allow the keratinous substrates to retain desirable cosmetic and aesthetic attributes.

BACKGROUND OF THE DISCLOSURE

When keratinous substrates such as hair and skin are exposed to environmental conditions, the substrates can lose many of their desirable properties. For example, hair can lose its shine, it can become frizzy or unmanageable, it can lose its color and it can become dry and brittle. Skin can also become dry and rough under low humidity conditions.

One method of maintaining desirable properties on hair and skin is to provide a protective barrier that will serve to seal such desirable benefits on the surface of hair and skin. For example, under low humidity conditions, hair can dry out and dried-out hair tends to be less shiny and more brittle. A protective barrier on the hair will help to keep moisture in the hair allowing it to keep its shine. Such a protective barrier can result in less hair damage, more shine and an overall healthy appearance of the hair.

Conversely, under high humidity conditions, hair tends to absorb water causing it to lose its shape and become unmanageable and unattractive. A protective barrier on the hair will help keep moisture out of the hair under high humidity conditions leading to improved manageability.

Thus, it is desirable to develop products that provide a protective barrier on the surface of hair that will allow the hair to retain moisture under low humidity conditions as well as prevent unwanted moisture from penetrating the hair under high humidity conditions. Such products can also help impart shine to hair and keep the hair shiny and healthy-looking for extended periods of time.

Such a protective barrier can also inhibit the loss of color from the surface of keratinous substrates such as hair. For example, a protective barrier can inhibit color fading in artificially colored hair generally attributed to environmental conditions such as high and low humidity, sunlight or from handling, everyday activities and washing. The protective barrier should preferably be water-resistant and/or transfer-resistant so that the barrier is not easily removed from the keratinous substrate through normal activities. Accordingly, it is desirable to develop products that provide a protective barrier on hair that will seal the color of artificially colored hair and help the hair retain its color for longer periods of time.

BRIEF SUMMARY OF THE DISCLOSURE

The present disclosure is directed to a composition comprising:
(a) at least one polyacid;
(b) at least one amino compound chosen from alkyl monoamines, alkoxylated polyamines, alkoxylated monoamines, polyamines and mixtures thereof; and
(c) a cosmetically acceptable carrier; and
wherein the alkyl monoamines of (b) are chosen from:
compounds corresponding to formula (IA):

$$RN(R')_2 \quad\quad\quad (IA)$$

wherein
R is a hydrocarbon radical containing at least 6 carbon atoms;
R' is H or a hydrocarbon radical containing less than 6 carbon atoms;
compounds corresponding to formula (IIA):

$$RCONHR'N(R'')_2 \quad\quad\quad (IIA)$$

wherein:
R is a hydrocarbon radical containing at least 6 carbon atoms;
R' is a divalent hydrocarbon radical containing less than 6 carbon atoms; and
R" is H or a hydrocarbon radical containing less than 6 carbon atoms; and
aminosilicones having one amino group.

The present disclosure is also directed to a method of sealing the surface of a keratinous substrate comprising:
(a) providing a composition comprising:
(i) at least one polyacid;
(ii) at least one amino compound chosen from alkyl monoamines, alkoxylated polyamines, alkoxylated monoamines, polyamines and mixtures thereof; and
(iii) a cosmetically acceptable carrier; and
(b) applying said composition to the surface of the keratinous substrate; and
wherein the alkyl monoamines of (a)(ii) are chosen from:
compounds corresponding to formula (IA):

$$RN(R')_2 \quad\quad\quad (IA)$$

wherein
R is a hydrocarbon radical containing at least 6 carbon atoms;
R' is H or a hydrocarbon radical containing less than 6 carbon atoms;
compounds corresponding to formula (IIA):

$$RCONHR'N(R'')_2 \quad\quad\quad (IIA)$$

wherein:
R is a hydrocarbon radical containing at least 6 carbon atoms;
R' is a divalent hydrocarbon radical containing less than 6 carbon atoms; and
R" is H or a hydrocarbon radical containing less than 6 carbon atoms; and
aminosilicones having one amino group.

DETAILED DESCRIPTION OF THE DISCLOSURE

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

Other than in the operating examples, or where otherwise indicated, all numbers expressing quantities of ingredients and/or reaction conditions are to be understood as being modified in all instances by the term "about" which encompasses ±10%.

"At least one" as used herein means one or more and thus includes individual components as well as mixtures/combinations thereof.

"Keratinous substrate" may be chosen from, for example, hair, skin, eyelashes, eyebrows, lips and nails.

The term "lipophilic" means those compounds which are soluble in oils and are either completely or partially insoluble in water. In accordance with the present disclosure, the solubility of the lipophilic compounds is preferably less than 5% by weight, more preferably less than 1% by weight, even more preferably less than 0.5% by weight and better still, less than 0.1% by weight in water at 25° C. and at atmospheric pressure.

The term "stable" as used herein means that the composition does not exhibit phase separation.

The term "sealing" (and its grammatical variations) as used herein means to provide a protective barrier over the exterior of a keratinous substrate in order to inhibit water from penetrating into and escaping from the keratinous substrate.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Alkoxylated" as used herein means comprising at least one alkoxy group. As used herein, an alkoxy group is a group corresponding to the formula —O—CHR—(CH2)n-, wherein R represents H or a C1-C5 alkyl group, and wherein n is an integer ranging from 1 to 6.

It has been surprisingly and unexpectedly discovered that the above-disclosed composition and method provided a protective barrier on hair that helped seal the color of artificially colored hair and helped the hair retain its color for longer periods of time. Moreover, when the above-disclosed compositions additionally contained an auxiliary ingredient chosen from cationic polymers, the resulting compositions allowed the hair to retain moisture under low humidity conditions as well as prevent unwanted moisture from penetrating the hair under high humidity conditions, thereby reducing or inhibiting frizz on hair. When the auxiliary ingredient was chosen from lipophilic compounds, the above-disclosed composition and method also helped to impart desirable shine to hair and keep the hair shiny and healthy-looking for extended periods of time.

Polyacids

The polyacids of the present disclosure are polymers derived from at least one of a sulfonic acid, carboxylic acid or phosphoric acid and generally have a number-average molecular mass ranging from 500 to 5,000,000.

The polyacids for use in the present disclosure may be chosen from aliphatic, cycloaliphatic and aromatic polyacids, unsaturated polyacids, and associative polyacids.

The carboxylic groups may be provided, for example, by unsaturated monocarboxylic or dicarboxylic acid monomers such as those corresponding to formula (I):

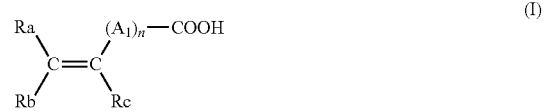

in which:
n is an integer ranging from 0 to 10,
A1 is chosen from methylene groups, optionally connected to the carbon atom of the unsaturated group, or to the neighboring methylene group when n is greater than 1, via a hetero atom such as oxygen and sulfur,
Ra is chosen from hydrogen phenyl groups, and benzyl groups,
Rb is chosen from hydrogen, (C1-4)alkyl groups, for example, methyl and ethyl, and carboxyl groups, and
Rc is chosen from hydrogen, lower alkyl groups, —CH2-COOH groups, phenyl groups, and benzyl groups.

Suitable polymers comprising carboxylic groups include, for example:

A) acrylic or methacrylic acid homo- and copolymers, and salts thereof, for example, the products sold under the names Versicol E and K by Allied Colloid and Ultrahold by BASF, copolymers of acrylic acid and of acrylamide, and sodium salts of polyhydroxycarboxylic acid;

B) copolymers of acrylic or methacrylic acid with a monoethylenic monomer such as ethylene, styrene, vinyl esters, acrylic or methacrylic acid esters, optionally grafted onto a polyalkylene glycol such as polyethylene glycol and optionally crosslinked. Such polymers are described, for example, in French Patent No. 1 222 944 and German Patent Application No. 2 330 956, the copolymers of this type comprising an optionally N-alkylated and/or hydroxyalkylated acrylamide unit in their chain as described, for example, in Luxembourg Patent Application Nos. 75370 and 75371. Other examples include copolymers of acrylic acid and of C1-C4 alkyl methacrylate and terpolymers of vinylpyrrolidone, of acrylic acid and of methacrylate of C1-C20 alkyl, for example of lauryl, such as the product sold by ISP under the name Acrylidone LM and methacrylic acid/ethyl acrylate/tert-butyl acrylate terpolymers such as the product sold under the name Luvimer 100 P by BASF;

C) copolymers derived from crotonic acid such as those comprising vinyl acetate or propionate units in their chain and optionally other monomers such as allylic esters or methallylic esters, vinyl ether or vinyl ester of a linear or branched saturated carboxylic acid with a long hydrocarbon-based chain such as those comprising at least 5 carbon atoms, it being possible for these polymers optionally to be grafted and crosslinked, or alternatively another vinyl, allylic or methallylic ester monomer of an alpha- or beta-cyclic carboxylic acid. Such polymers are described, for example, in French Patent Nos. 1 222 944, 1 580 545, 2 265 782, 2 265 781, 1 564 110, and 2 439 798. A non-limiting example of a suitable commercial product is the resin 28-29-30 sold by National Starch;

D) copolymers derived from C4-C8 monounsaturated carboxylic acids chosen from:
copolymers comprising (i) at least one entity chosen from maleic, fumaric, and itaconic acids and anhydrides and (ii) at least one monomer chosen from vinyl esters, vinyl ethers, vinyl halides, phenylvinyl derivatives, and acrylic acid and its esters, the acid functions of these copolymers optionally being monoesterified or monoamidated. Such polymers are described, for example, in U.S. Pat. Nos. 2,047,398, 2,723, 248, and 2,102,113 and British Patent No. 839 805. Suitable commercial products include, for example, those sold under the names Gantrez S and ES by ISP,
copolymers comprising (i) at least one unit chosen from maleic, citraconic, and itaconic acid units and (ii) at least one monomer chosen from allylic or methallylic esters optionally comprising at least one group chosen from acrylamide, methacrylamide, and alpha-olefin groups, acrylic esters, methacrylic esters, acrylic acids, methacrylic acids, and vinylpyrrolidone in their chain,
the acid functions of these copolymers optionally being monoesterified or monoamidated.

These polymers are described, for example, in French Patent Nos. 2 350 384 and 2 357 241;
E) polyacrylamides comprising carboxylate groups; and
F) anionic polyurethanes, such as the product sold by BASF under the name Luviset PUR.

The polymers comprising sulfonic groups may be polymers comprising vinylsulfonic, styrenesulfonic, naphthalenesulfonic, and/or acrylamidoalkylsulfonic units.

These polymers may be chosen, for example, from: polyvinylsulfonic acid salts having a molecular weight ranging from 1000 to 100,000, as well as copolymers with an unsaturated comonomer such as acrylic or methacrylic acids and their esters, as well as acrylamide and its derivatives, vinyl ethers, and vinylpyrrolidone;
polystyrenesulfonic acid salts, such as the sodium salts sold, for example, under the name Flexan 130 by National Starch. These compounds are described, for example, in French Patent No. 2 198 719;
polyacrylamidesulfonic acid salts, such as those mentioned in U.S. Pat. No. 4,128,631, for example, polyacrylamidoethylpropanesulfonic acid.

According to the present disclosure, the polymers may be chosen from those of grafted silicone type comprising a polysiloxane portion and a portion consisting of a non-silicone organic chain, one of the two portions constituting the main chain of the polymer, the other being grafted onto the said main chain. These polymers are described, for example, in European Patent Application Nos. 0 412 704, 0 412 707, 0 640 105, and 0 582 152, International Patent Application Publication Nos. WO 95/00578 and WO 93/23009, and U.S. Pat. Nos. 4,693,935, 4,728,571, and 4,972,037.

Such polymers may include, for example, copolymers that can be obtained by radical polymerization from a monomer mixture comprising:
a) 50 to 90 percent by weight of tert-butyl acrylate;
b) 0 to 40 percent by weight of acrylic acid;
c) 5 to 40 percent by weight of silicone macromer of formula (II):

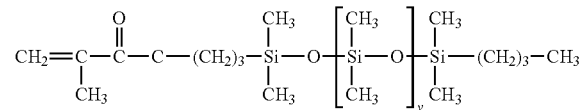

(II)

with v being a number from 5 to 700; the weight percentages being calculated relative to the total weight of the monomers.

Other examples of grafted silicone polymers include, but are not limited to, polydimethylsiloxanes (PDMSs) onto which are grafted, via a thiopropylene-type connecting chain, mixed polymer units of the poly(meth)acrylic acid type and of the polyalkyl(meth)acrylate type and polydimethylsiloxanes (PDMSs) onto which are grafted, via a thiopropylene-type connecting chain, polymer units of the polyisobutyl(meth)acrylate type.

In one embodiment, functionalized silicone or non-silicone polyurethanes may also be used as film-forming polymers. Examples of suitable polyurethanes include those disclosed in European Patent Nos. 0 751 162, 0 637 600, 0 648 485, 0 619 111, and 0 656 021, French Patent No. 2 743 297, and International Patent Application Publication No. WO 94/03510.

According to another embodiment of the present disclosure, the polymers may be chosen from acrylic acid copolymers, such as the acrylic acid/ethyl acrylate/N-tert-butylacrylamide terpolymers sold under the name Ultrahold Strong by BASF, copolymers derived from crotonic acid, such as vinyl acetate/vinyl tert-butylbenzoate/crotonic acid terpolymers and the crotonic acid/vinyl acetate/vinyl neododecanoate terpolymers sold under the name Resin 28-29-30 by National Starch, polymers derived from maleic, fumaric, or itaconic acids with isobutylene, vinyl esters, vinyl ethers, vinyl halides, phenylvinyl derivatives and acrylic acid and esters thereof, such as the methyl vinyl ether/monoesterified maleic acid copolymers sold, for example, under the name Gantrez by ISP, the copolymers of methacrylic acid and of methyl methacrylate sold under the name Eudragit L by Rohm Pharma, the copolymers of methacrylic acid and of ethyl acrylate sold under the name Luvimer MAEX and MAE by BASF, the vinyl acetate/crotonic acid copolymers and the vinyl acetate/crotonic acid copolymers grafted with polyethylene glycol sold under the name Aristoflex A by BASF, and the polyurethane Luviset PUR sold by BASF.

The polymers may, in at least one embodiment, be chosen from the methyl vinyl ether/monoesterified maleic acid copolymers sold under the name Gantrez ES 425 by ISP, the acrylic acid/ethyl acrylate/N-tert-butylacrylamide terpolymers sold under the name Ultrahold Strong by BASF, the copolymers of methacrylic acid and of methyl methacrylate sold under the name Eudragit L by Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by National Starch, the copolymers of methacrylic acid and of ethyl acrylate sold under the name Luvimer MAEX and MAE by BASF, the vinylpyrrolidone/acrylic acid/lauryl methacrylate terpolymers sold under the name Acrylidone LM by ISP, and the polyurethane Luviset PUR sold by BASF.

The polyacid of the present disclosure may also include, for example, those polymers comprising units B and C distributed randomly in the polymer chain, in which B denotes a unit derived from a monomer comprising at least one basic nitrogen atom and C denotes a unit derived from an acid monomer comprising at least one group chosen from carboxylic and sulfonic groups, or alternatively B and C may denote groups derived from monomers chosen from carboxybetaine and sulfobetaine zwitterionic monomers.

B and C may also denote a cationic polymer chain comprising primary, secondary, tertiary, and/or quaternary amine groups, in which at least one of the amine groups bears a carboxylic or sulfonic group connected via a hydrocarbon-based group or alternatively B and C form part of a chain of a polymer containing an alpha-dicarboxylic ethylene unit in which one of the carboxylic groups has been made to react with a polyamine containing one or more primary or secondary amine groups.

Non-limiting examples of polymers corresponding to the definition given above include:

(1) polymers resulting from the copolymerization of a monomer derived from a vinyl compound comprising a carboxylic group such as acrylic acid, methacrylic acid, maleic acid, and alpha-chloroacrylic acid, and a basic monomer derived from a substituted vinyl compound comprising at least one basic atom (for example, an amino function), such as dialkylaminoalkyl methacrylate and acrylate, and dialkylaminoalkylmethacrylamides and dialkylaminoalkylacrylamides. Such compounds are described, for example, in U.S. Pat. No. 3,836,537. A non-limiting example of a commercially available product is the sodium acrylate/acrylamidopropyl trimethylammonium chloride copolymer sold under the name Polyquart KE 3033 by Henkel.

The vinyl compound may also be a dialkyldiallylammonium salt such as diethyldiallylammonium chloride. The copolymers of acrylic acid and of the latter monomer are sold, for example, under the names Merquat 280, Merquat 295, and Merquat Plus 3330 by Calgon.

(2) polymers comprising units derived from:
a) at least one monomer chosen from acrylamides and methacrylamides substituted on the nitrogen atom with an alkyl group,
b) at least one acidic comonomer comprising at least one reactive carboxylic group, and
c) at least one basic comonomer such as esters containing primary, secondary, tertiary, and quaternary amine substituents of acrylic and methacrylic acids and the product of quaternization of dimethylaminoethyl methacrylate with dimethyl or diethyl sulfate.

The N-substituted acrylamides or methacrylamides may include compounds in which the alkyl groups comprise from 2 to 12 carbon atoms, for example, N-ethylacrylamide, N-tert-butylacrylamide, N-tert-octylacrylamide, N-octylacrylamide, N-decylacrylamide, N-dodecylacrylamide, and the corresponding methacrylamides.

The acidic comonomers may be chosen, for example, from acrylic acid, methacrylic acid, crotonic acid, itaconic acid, maleic acid, fumaric acid, and alkyl monoesters, comprising from 1 to 4 carbon atoms, of maleic or fumaric acids and anhydrides.

Suitable basic comonomers include, for example, aminoethyl, butylaminoethyl, N,N'-dimethylaminoethyl, and N-tert-butylaminoethyl methacrylates.

A further non-limiting example is the copolymer whose CTFA (4th edition, 1991) name is octylacrylamide/acrylates/butylaminoethyl methacrylate copolymer, such as the products sold under the names Amphomer and Lovocryl 47 by National Starch.

(3) crosslinked and acylated polyamino amides partially or totally derived from polyamino amides of formula (III):

$$\text{\{CO—R}_{10}\text{—CO—Z\}}\tag{III}$$

in which:
R10 is chosen from divalent groups derived from a saturated dicarboxylic acid, mono- or dicarboxylic aliphatic acids comprising an ethylenic double bond, esters of lower alkanols, comprising from 1 to 6 carbon atoms, of these acids, and groups derived from the addition of any one of said acids to a bis(primary) or bis(secondary)amine, and
Z is a group derived from a bis(primary), mono- or bis(secondary) polyalkylene-polyamine and, in at least one embodiment, may represent:
a) in an amount ranging from 60 to 100 mol %, the group

$$\text{—NH—\{(CH}_2)_x\text{—NH\}}_p\tag{IV}$$

where x=2 and p=2 or 3, or alternatively, x=3 and p=2
this group being derived from diethylenetriamine, from triethylenetetraamine, or from dipropylenetriamine;
b) in an amount ranging from 0 to 40 mol %, the group (IV) above in which x=2 and p=1 and which is derived from ethylenediamine, or the group derived from piperazine:

c) in an amount ranging from 0 to 20 mol %, the
—NH—(CH$_2$)$_6$—NH— group derived from hexamethylenediamine, these polyamino amides being crosslinked by addition reaction of a difunctional crosslinking agent chosen from epihalohydrins, diepoxides, dianhydrides, and bis-unsaturated derivatives, using from 0.025 to 0.35 mol of crosslinking agent per amine group of the polyamino amide and acylated by the action of an entity chosen from acrylic acid, chloroacetic acid, an alkane sultone, and salts thereof.

The saturated carboxylic acids may be chosen from acids comprising from 6 to 10 carbon atoms, such as adipic acid, 2,2,4-trimethyladipic acid, 2,4,4-trimethyladipic acid, terephthalic acid, and acids comprising an ethylenic double bond, for instance acrylic acid, methacrylic acid, and itaconic acid.

The alkane sultones used in the acylation may be chosen, for example, from propane sultone and butane sultone, and the salts of the acylating agents may be chosen from sodium and potassium salts.

(4) polymers comprising zwitterionic units of formula (V):

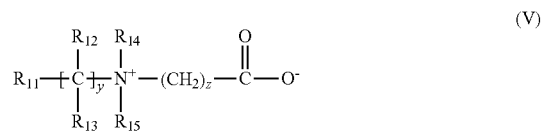

in which:

R1 is a polymerizable unsaturated group, for example, an acrylate, methacrylate, acrylamide, and methacrylamide group, y and z, which may be identical or different, are integers ranging from 1 to 3, R12 and R13, which may be identical or different, are chosen from hydrogen and methyl, ethyl, and propyl groups, and R14 and R15, which may be identical or different, are chosen from hydrogen and alkyl groups such that the sum of the carbon atoms in R14 and R15 does not exceed 10.

The polymers comprising such units may also contain units derived from nonzwitterionic monomers such as dimethylaminoethyl acrylate, dimethylaminoethyl methacrylate, diethylaminoethyl acrylate, diethylaminoethyl methacrylate, alkyl acrylates, alkyl methacrylates, acrylamides, methacrylamides, and vinyl acetate. Non-limiting example of such copolymers include butyl methacrylate/N,N-dimethylcarboxyaminoethyl methacrylate copolymers.

(5) polymers derived from chitosan comprising monomer units chosen from units of formulae (D)-(F):

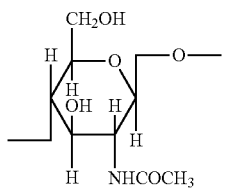 (D)

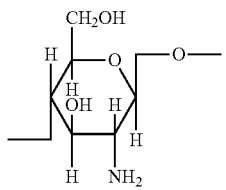 (E)

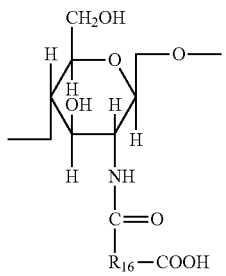 (F)

the unit (D) being present in an amount ranging from 0% to 30%, the unit (E) in an amount ranging from 5% to 50%, and the unit (F) in an amount ranging from 30% to 90%, it being understood that, in this unit (F), R16 is a group of formula:

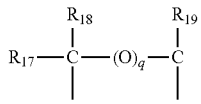

in which, if q=0, R17, R18, and R19, which may be identical or different, are chosen from hydrogen, methyl, hydroxyl, acetoxy, and amino residues, monoalkylamine residues and dialkylamine residues that are optionally interrupted by at least one nitrogen atom and/or optionally substituted with at least one group chosen from amine, hydroxyl, carboxyl, alkylthio, and sulfonic groups, alkylthio residues in which the alkyl group comprises an amino residue, at least one of the groups R17, R18, and R19 being, in this case, a hydrogen atom;
or, if q=1, R17, R18, and R19 are each hydrogen atoms,
as well as the acid and base addition salts of these compounds.
(6) polymers described, for example, in French Patent No. 1 400 366 and comprising the repeating unit of formula (VI):

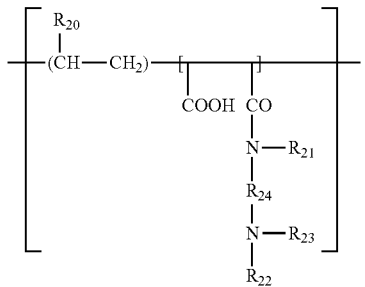 (VI)

in which:
R20 is chosen from hydrogen, CH$_3$O, CH$_3$CH$_2$O, and phenyl groups,
R21 is chosen from hydrogen and lower alkyl groups such as methyl and ethyl,
R22 is chosen from hydrogen and C$_1$-C$_6$ lower alkyl groups such as methyl and ethyl,
R24 is chosen from —CH2-CH2-, —CH2-CH2-CH2-, and —CH2-CH(CH3)- groups, and
R23 is chosen from C1-C6 lower alkyl groups such as methyl and ethyl and groups corresponding to the formula:
—R24-N(R22)2-, wherein R24 is chosen from —CH2-CH2-, —CH2-CH2-CH2-, and —CH2-CH(CH3)- groups, and R22 has the definition given above.
(7) polymers derived from the N-carboxyalkylation of chitosan, such as N-carboxymethylchitosan and N-carboxybutylchitosan.
(8) amphoteric polymers of the type -D-X-D-X chosen from:
a) polymers obtained by the action of chloroacetic acid or sodium chloroacetate on compounds containing at least one unit of formula:

-D-X-D-X-D- (VII)

wherein D denotes a group

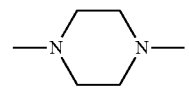

and X is chosen from the symbols E or E', wherein E or E', which may be identical or different, are chosen from divalent groups that are alkylene groups comprising a straight or branched chain comprising up to 7 carbon atoms in the main chain, which is unsubstituted or substituted with hydroxyl groups and which may contain, in addition to oxygen, nitrogen, and sulfur atoms, 1 to 3 aromatic and/or heterocyclic rings; the oxygen, nitrogen, and sulfur atoms being present in the form of an entity chosen from ether, thioether, sulfoxide, sulfone, sulfonium, alkylamine, and alkenylamine groups, hydroxyl, benzylamine, amine oxide, quaternary ammonium, amide, imide, alcohol, ester, and/or urethane groups.
b) polymers of formula:

-D-X-D-X- (VII')

wherein D denotes a group

and X is chosen from the symbols E and E', and at least once E'; E having the meaning given above and E' being a divalent group that is an alkylene group with a straight or branched chain having up to 7 carbon atoms in the main chain, which is unsubstituted or substituted with at least one hydroxyl group and containing at least one nitrogen atom, the nitrogen atom being substituted with an alkyl chain that is optionally interrupted by an oxygen atom and comprising at least one carboxyl function or at least one hydroxyl function and betainized by reaction with an entity chosen from chloroacetic acid and sodium chloroacetate.
(9) (C1-C5) alkyl vinyl ether/maleic acid copolymers partially modified by semiamidation with an N,N-dialkylaminoalkylamine such as N,N-dimethylaminopropylamine or by semiesterification with an N,N-dialkylaminoalkynol. These copolymers may also contain other vinyl comonomers such as vinylcaprolactam.

The polyacid of the present disclosure may also be chosen from silicone acids such as polysilicone-8 (3M brand silicones "Plus" polymer VS 80, commercially available from 3M company) which has the structure:

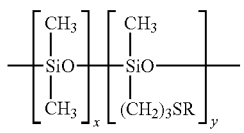

where R represents the acrylates copolymer radical.

In one embodiment of the present disclosure, the polyacid is preferably chosen from those of the family (3), such as the copolymer whose CTFA name is octylacrylamide/acrylates/butylaminoethyl methacrylate copolymer, for example, which is sold under the names Amphomer, Amphomer LV 71, and Lovocryl 47 by National Starch and those of the family (4), such as butyl methacrylate/N,N-dimethylcarboxyaminoethyl methacrylate copolymers.

In another embodiment of the present disclosure, the polyacid is preferably chosen from VA/crotonates copolymer (and) isopropyl alcohol, Butyl ester of PVM/MA copolymer, isopropyl ester of PVM/MA copolymer, Ethyl ester of PVM/MA copolymer, VA/crotonates/vinyl neodecanoate copolymer, VA/crotonates copolymer, Ethylene/acrylic acid copolymer, VA/vinyl butyl benzoate/crotonates copolymer, Acrylates/octylacrylamide copolymer, Acrylates/t-Butylacrylamide copolymer, VP/acrylates/lauryl methacrylate copolymer, Styrene/acrylates copolymer, Acrylates copolymer, Polyacrylate-3, Carbomer, Acrylates/C10-30 alkyl acrylate crosspolymer and mixtures thereof.

The at least one polyacid is preferably present in the composition in an amount of from about 0.01% to about 20% by weight, more preferably from about 0.1% to about 10% by weight, and even more preferably from about 0.5% to about 8% by weight, based on the total weight of the composition.

Alkyl Monoamines

The alkyl monoamines of the present disclosure are amine compounds having one amino group.

Non-limiting examples of preferred alkyl monoamines include aliphatic amine compounds corresponding to formula (IA) and their salts:

$$RN(R')_2 \quad (IA)$$

wherein

R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and the groups R', which may be identical or different, represent H or a hydrocarbon radical containing less than 6 carbon atoms. In addition, the groups R', which may be identical or different, are linear or branched, acyclic or cyclic, saturated or unsaturated, substituted or unsubstituted. Preferably, the groups R', which may be identical or different, are H or a methyl group.

Preferred alkyl monoamines include, but are not limited to the following examples: dimethyl lauramine, dimethyl behenamine, dimethyl cocamine, dimethyl myristamine, dimethyl palmitamine, dimethyl stearamine, dimethyl tallowamine, dimethyl soyamine, stearamine, soyamine, cocamine, lauramine, palmitamine, oleamine, tallow amine and mixtures thereof.

Other non-limiting examples of preferred alkyl monoamines include amidoamine compounds corresponding to formula (IIA) and their salts:

$$RCONHR'N(R'')_2 \quad (IIA)$$

wherein:

R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and R' is a divalent hydrocarbon radical containing less than 6 carbon atoms, preferably 2 or 3 carbon atoms, and R'' is H or a hydrocarbon radical containing less than 6 carbon atoms. In addition, R'' is linear or branched, acyclic or cyclic, saturated or unsaturated, substituted or unsubstituted. Typically, R'' is a linear or branched, acyclic alkyl or alkenyl group. Preferably, R'' is H or a methyl group.

Other non-limiting examples of preferred alkyl monoamines also include aminosilicones having one amino group such as aminopropyl phenyl trimethicone.

Preferred amidoamines include, but are not limited to the following examples: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, and mixtures thereof.

The at least one alkyl monoamine can be present in the composition of the present disclosure in an amount of from about 0.1 to about 50% by weight, preferably from about 0.5 to about 30% by weight, and more preferably from about 1 to about 20% by weight, based on the total weight of the composition.

Alkoxylated Polyamines

The alkoxylated polyamines of the present disclosure are chosen from amine compounds having at least two amino groups and at least one degree of alkoxylation. The alkoxylation is provided by an alkylene oxide group which is preferably chosen from ethylene oxide and propylene oxide.

Non-limiting preferred examples of suitable alkoxylated polyamines include compounds corresponding to formula (IB):

$$NH_2R(R'CHCH_2O)_x(R'CHCH_2O)_y(R'CHCH_2O)_zRNH_2 \quad (IB)$$

wherein R represents a —CH2-, —CH$_2$CH$_2$—, —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted;

x, y, and z independently of one another, represent numbers of from 0 to about 100;

R' represents hydrogen, or an alkyl group, preferably a methyl group; and

The sum of x+y+z is at least 1.

In formula (IB), R is preferably a linear or branched, acyclic alkyl or alkenyl group or an alkyl phenyl group; x, y, and z independently of one another, preferably represent numbers ranging from 2 to 100.

Examples of the alkoxylated polyamines for use in the present disclosure which correspond to formula (IB) include, for example, tetradecyloxypropyl-1,3-diaminopropane; a $C_{12-14}$ alkyl oxypropyl-1,3-diaminopropane; a $C_{12-15}$ alkyloxypropyl amine and other similar materials that are commercially available from Tomah under the tradename of TOMAH® DA-17.

Other examples of alkoxylated polyamines of Formula (IB) are diamine compounds belonging to the Jeffamine series such as the Jeffamine® D and Jeffamine® ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. Jeffamine® D series compounds are amine terminated PPGs (polypropylene glycols) and Jeffamine® ED series compounds are polyether diamine based with a predominantly PEG (polyethylene glycol) backbone.

Other non-limiting preferred examples of suitable alkoxylated polyamines in the diamine form include compounds corresponding to formula (IIB):

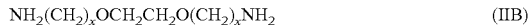

$$NH_2(CH_2)_xOCH_2CH_2O(CH_2)_xNH_2 \quad \text{(IIB)}$$

wherein x is 2 or 3.

Examples of alkoxylated polyamines of Formula (IIB) are diamine compounds belonging to the JEFFAMINE series available from Huntsman Corporation, Salt Lake City, Utah, such as JEFFAMINE EDR148, and JEFFAMINE EDR176.

Additional non-limiting preferred examples of alkoxylated polyamines in the triamine form include compounds corresponding to formula (IIIB):

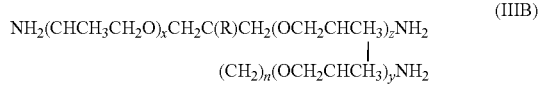

$$NH_2(CHCH_3CH_2O)_xCH_2C(R)CH_2(OCH_2CHCH_3)_zNH_2$$
$$(CH_2)_n(OCH_2CHCH_3)_yNH_2 \quad \text{(IIIB)}$$

wherein R is hydrogen, —CH$_2$ or —C$_2$H$_5$, n=0 or 1, and x, y, and z independently of one another, represent numbers of from 0 to 100 and the sum of x+y+z is at least 1.

Examples of alkoxylated polyamines for use in the present disclosure which correspond to formula (IIIB) are triamine compounds belonging to the Jeffamine series such as the Jeffamine® T series available from Huntsman Corporation, Salt Lake City, Utah. Examples of the Jeffamine® T series compounds are JEFFAMINE T403, JEFFAMINE T3000, and JEFFAMINE T5000. Jeffamine® T series compounds are triamines made by reacting PO with a triol initiator followed by aminating the terminal hydroxyl groups.

Another type of preferred alkoxylated polyamines include compounds of formulas (IVB) and (VB) hereunder:

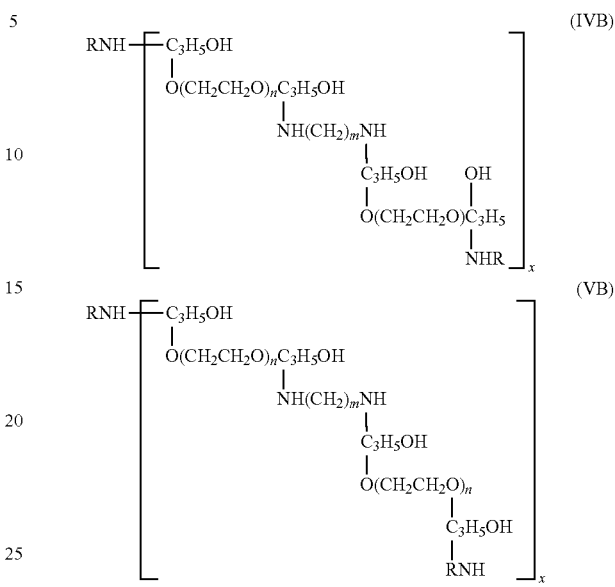

wherein

R in formula (IVB) represents the alkyl group derived from tallow and R in formula (VB) represents the alkyl group derived from coconut oil;

n in both formulas (IVB) and (VB) has a total value ranging from 10 to 20;

m in both formulas (IVB) and (VB) has a value ranging from 2 to 6; and x in both formulas (IVB) and (VB) has a value ranging from 2 to 4.

Other preferred types of alkoxylated polyamines include aminosilicones with at least one degree of alkoxylation.

Preferred examples of alkoxylated polyamines for use in the present disclosure include compounds of Formulas (IVB) and (VB) above. such as PEG-15 Tallow Polyamine and PEG-15 Cocopolyamine, respectively.

The at least one alkoxylated polyamine can be present in the composition of the present disclosure in an amount of from about 0.1 to about 50% by weight, preferably from about 0.5 to about 15% by weight, more preferably from about 0.5 to about 10% by weight, based on the total weight of the composition.

Alkoxylated Monoamines

The alkoxylated monoamines of the present disclosure are chosen from amine compounds having at one amino groups and at least one degree of alkoxylation. The alkoxylation is provided by an alkylene oxide group which is preferably chosen from ethylene oxide and propylene oxide.

Non-limiting preferred examples of suitable alkoxylated monoamines include compounds corresponding to the formula (IC):

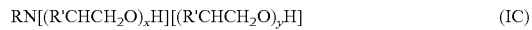

$$RN[(R'CHCH_2O)_xH][(R'CHCH_2O)_yH] \quad \text{(IC)}$$

wherein R is a hydrocarbon radical containing at least 6 carbon atoms. R can be linear or branched, acyclic or cyclic, saturated or unsaturated, aliphatic or aromatic, substituted or unsubstituted;

x and y, independently of one another, represent numbers of from 0 to 100 provided that the sum of x+y is >0;

the groups R', which may be identical or different, represent hydrogen, or an alkyl group such as a methyl group.

Typically, R is a linear or branched, acyclic alkyl or alkenyl group or an alkyl phenyl group; x and y, independently of one another, are each typically a number from 0 to 30. Typically, one R' group is hydrogen, and the other one is methyl.

Examples of preferred alkoxylated monoamines for use in the present disclosure which correspond to formula (IC) are PEG-2 Cocamine, PEG-3 Cocamine, PEG-5 Cocamine, PEG-10 Cocamine, PEG-15 Cocamine, PEG-20 Cocamine, PEG-2 Lauramine, PEG-12 Palmitamine, PEG-2 Rapeseed-amine, PEG-2 Oleamine, PEG-5 Oleamine, PEG-6 Oleamine, PEG-10 Oleamine, PEG-15 Oleamine, PEG-20 Oleamine, PEG-25 Oleamine, and PEG-30 Oleamine. Other examples are alkoxylated derivatives of soyamine, stearamine and tallow amine.

Other non-limiting examples of suitable alkoxylated monoamines include compounds corresponding to formula (IIC):

$$RNR''[(R'CHCH_2O)_xH] \quad (IIC)$$

wherein R is a hydrocarbon radical containing at least 6 carbon atoms. R can be linear or branched, acyclic or cyclic, saturated or unsaturated, aliphatic or aromatic, substituted or unsubstituted;
x represents a number of from 1 to 100;
R' represents hydrogen, or an alkyl group such as in particular a methyl group; and
R" is a hydrogen or a hydrocarbon radical.

Typically, R is a linear or branched, acyclic alkyl or alkenyl group or an alkyl phenyl group; x is typically a number from 1 to 30.

When R" in formula (IIC) is a hydrocarbon radical group, this group may be linear or branched, saturated or unsaturated, substituted or unsubstituted. The hydrocarbon radical represented by R" may also contain an alkoxylated moiety (as defined by [(R'CHCH$_2$O)$_y$H]), and/or heteroatoms such as nitrogen. When R" contains at least one alkoxylated moiety, the total number of alkoxylation in the formula may range from 1 to 120.

Examples of alkoxylated monoamines for use in the present disclosure which correspond to formula (IIC) are PEG-3 Tallow Aminopropylamine, PEG-10 Tallow Aminopropylamine, PEG-15 Tallow Aminopropylamine, and PEG-105 Behenyl Propylenediamine.

Additional non-limiting examples of alkoxylated monoamines include compounds corresponding to formula (IIIC):

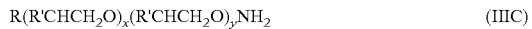

$$R(R'CHCH_2O)_x(R'CHCH_2O)_yNH_2 \quad (IIIC)$$

wherein R is a hydrocarbon radical containing at least 6 carbon atoms. R can be linear or branched, acyclic or cyclic, saturated or unsaturated, aliphatic or aromatic, substituted or unsubstituted;
x and y, independently of one another, represent numbers of from 0 to 100 with the proviso that the sum of x+y is >0;
the groups R', which may be identical or different, represent hydrogen, or an alkyl group such as in particular a methyl group.

Typically, R is a linear or branched, acyclic alkyl or alkenyl group or an alkyl phenyl group; x and y, independently of one another, are each typically a number from 0 to 30.

Examples of alkoxylated monoamines for use in the present disclosure which correspond to formula (IIIC) are polyetheramines containing a monoamine group. These polyetheramines are commercially available from Hunstman under the tradename Jeffamine (M series such as M-600, M-1000, M-2005 and M-2070) and Surfonamine series (B-60, B-100, B-200, L-100, L-200, L-207, L-300).

The alkoxylated monoamines for use in the present disclosure may also be chosen from aminosilicones having one amino group and at least one degree of alkoxylation.

The at least one alkoxylated monoamine can be present in the composition in an amount of from about 0.1 to about 50% by weight, preferably from about 0.5 to about 30% by weight, more preferably from about 1 to about 20% by weight, based on the total weight of the composition.

Polyamines

The polyamines may in particular be chosen from aminosilicones, polyvinylamines, aminated polysaccharides, amine substituted polyalkylene glycols, amine substituted polyacrylate crosspolymers, amine substituted polyacrylates, amine substituted polymethacrylates, proteins, protein derivatives, amine substituted polyesters, polyamino acids, polyalkylamines, diethylene triamine, triethylenetetramine, spermidine, spermine and mixtures thereof.

The polyamines for use in the present disclosure are preferably chosen from aminosilicones having at least two amino groups.

The polyamines of the present disclosure are also preferably chosen from polyvinylamines which are generally sold under the trade name Lupamines® 9095, 9030, 9010, 5095 and 1595 from BASF. One preferred example of such polyamines are high molecular weight polyvinlyamines sold under the trade name Lupamines® 9095.

Other preferred polyamines of the present disclosure include are amine substituted polyalkylene glycols such as PEG-15 cocopolyamine and PEG-15 Tallow Polyamine and amine substituted polyacrylate crosspolymer such as the product sold under the name Carbopol® Aqua CC polymer by Lubrizol Advanced Materials, Inc.

In one preferred embodiment of the present disclosure, the polyamine compound is chosen from PEG-15 Tallow Polyamine, PEG-15 Cocopolyamine, and mixtures, thereof.

The polyamine compound of the present disclosure may also be chosen from proteins and protein derivatives such as wheat protein, soy protein, oat protein, collagen, and keratin protein.

In another preferred embodiment of the present disclosure, the polyamine compound is chosen from compounds comprising lysine, compounds comprising arginine, compounds comprising histidine, and compounds comprising hydroxylysine. Non limiting examples include chitosan, and polyamino acids such as polyarginine and polylysine.

The at least one polyamine can be present in the composition of the present disclosure in an amount of from about 0.1 to about 50% by weight, preferably from about 0.25 to about 30% by weight, more preferably from about 0.5 to about 15% by weight, and even more preferably from about 0.5 to about 10% by weight, based on the total weight of the composition.

Preferably, the ratio of the acid number of the at least one polyacid to the total amine number of the amino compound(s) chosen from alkoxylated polyamines, alkyl monoamines, alkoxylated monoamines, polyamines and mixtures thereof is from about 1:30 to about 30:1, and more preferably is from about 1:20 to about 20:1 and, even more preferably is from about 1:10 to about 10:1.

Acid and amine numbers are generally determined by acid-base titration in the presence of a color indicator based on the European and American Pharmacopoeias and Standard ISO 660.

In one embodiment the ratio of acid number of the at least one polyacid to the total amine number of the amino compound(s) chosen from alkoxylated polyamines, alkyl monoamines, alkoxylated monoamines and mixtures thereof cannot be calculated because the at least one polyacid is in excess.

In another embodiment the ratio of acid number of the at least one polyacid to the total amine number of the amino compound(s) chosen from alkoxylated polyamines, alkyl monoamines, alkoxylated monoamines and mixtures thereof cannot be calculated because the at least one amino compound is in excess.

Cosmetically Acceptable Carrier

The cosmetically acceptable carrier can be water and/or an organic solvent. Suitable organic solvents include alcohols, such as ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, polybutene, hydrogenated polyisobutene, hydrogenated polydecene, polydecene, squalene, petrolatum and isoparaffins; and mixtures, thereof.

The inventive composition can comprise a cosmetically acceptable carrier in the amount of about 95%, 90%, 80%, 70%, 60%, 50%, 40%, 30%, 20%, 10%, 5% or less based on the total weight of the composition. The composition can comprise a cosmetically acceptable carrier in the amount of about 5%, 10%, 20%, 30%, 40%, 50%, 60%, 70%, 80%, 90%, 95%, or more based on the total weight of the composition. Additionally, the amount of cosmetically acceptable carrier can be any combination of the above values, for example from about 20% to about 95%, or from about 50% to about 60% by weight based on the total weight of the compositions.

Auxiliary Ingredients

The composition may optionally contain at least one auxiliary ingredient. The auxiliary ingredients may include in particular, lipophilic compounds, shine agents, film forming agents, conditioning agents, cationic polymers, nonionic surfactants, anionic surfactants, amphoteric surfactants, zwitterionic surfactants, skin active agents, sunscreens, viscosity modifiers, antibacterial agents, preservatives, pH adjusting agents, bleaching agents, hair dyeing agents, perfumes/fragrance agents, sequestering agents, anti-dandruff agents, and mixtures thereof.

The at least one lipophilic compound may, for example, be chosen from oils, fatty esters, hydrocarbon oils, silicones different from polyacids of the present disclosure, waxes, fatty acids and salts thereof, fatty alcohols, lipophilic vitamins and esters thereof, organic sunscreens, phospholipids, and mixtures thereof.

Non-limiting examples of oils include plant oils such as olive oil, avocado oil, coconut oil, safflower oil, almond oil, castor oil, jojoba oil, peanut oil, sesame oil, hazelnut oil, sunflower oil, apricot kernel oil, grapeseed oil, linseed oil and palm oil.

Non-limiting examples of synthetic oils and hydrocarbon oils include mineral oil, petrolatum, and C10-C40 hydrocarbons which may be aliphatic (with a straight, branched or cyclic chain), aromatic, arylaliphatic such as paraffins, isoparaffins, isododecanes, aromatic hydrocarbons, and mixtures thereof.

Non-limiting examples of silicones include phenyltrimethicone, dimethicone, cyclomethicone, dimethicone copolyol, laurylmethicone copolyol, cetyl dimethicone, dimethicone copolyol lactate, and polyorganosiloxanes such as polydimethylsiloxane.

Non-limiting examples of waxes include paraffin wax, beeswax, candelilla wax, carnauba wax, jasmine wax, jojoba wax and mimosa wax.

Suitable fatty acids include those containing from 8 to 30, preferably from 12 to 24 carbon atoms, and carboxylate salts of fatty acids. The sodium, potassium, ammonium, calcium and magnesium carboxylates of fatty acids listed are typical examples of the carboxylate salts of the fatty acids.

Non-limiting preferred examples of fatty alcohols include compounds of formula:

R—OH where R represents a hydrocarbon radical containing at least three carbon atoms, preferably from 8 to 30, more preferably from 12 to 24 carbon atoms, and which may be linear or branched, acyclic or cyclic, saturated or unsaturated, aliphatic or aromatic, substituted or unsubstituted. Typically, R is a linear or branched, acyclic alkyl or alkenyl group or an alkyl phenyl group.

Non-limiting preferred fatty esters include esters formed from fatty acids and C1-10 alcohols and esters formed from the fatty alcohols as defined hereabove and C1-10 carboxylic acids.

According to a preferred embodiment, the at least one lipophilic compound is chosen from isopropyl palmitate, capric/caprylic triglyceride, isodecyl neopentanoate, polylsobutylene, phloretin, ellagic acid, vitamin D, vitamin E, vitamin E acetate, vitamin A, vitamin A palmitate, 2-oleamido-1,3-octadecanediol, octyl methoxycinnamate, octyl salicylate, 18-methyleicosanoic acid, and mixtures thereof.

According to another preferred embodiment, the at least one lipophilic compound is chosen from plant oils, hydrocarbon oils, synthetic oils, fatty acids having at least 12 carbon atoms, fatty esters and mixtures thereof.

Non-limiting examples of film forming agents can be chosen from anionic compounds, non-ionic compounds, amphoteric compounds, zwitterionic compounds, proteins, viscosity modifiers, cationic polymers, polyamides, polyaminoamides, polyesters, silicone resins, polysaccharides, silicone fluids, polyacrylamides, starches, gums and mixtures thereof.

Non-limiting examples of conditioning agents include cationic conditioners such as quaternium-27, behenamidopropyl PG-dimonium chloride, hydroxyethyl tallowedimonium chloride, stearalkonium chloride and cetrimonium chloride.

Non-limiting examples of cationic polymers include hexadimethrine chloride, polyquaternium-4, polyquaternium-6, polyquaternium-7, polyquaternium-10, polyquaternium-11, polyquaternium-16, polyquaternium-22, polyquaternium-32 and guar hydroxyproyltrimonium chloride.

Non-limiting examples of nonionic surfactants includes alkoxylated derivatives of the following: fatty alcohols, alkyl phenols, fatty acids, fatty acid esters and fatty acid amides, wherein the alkyl chain is in the C12-50 range, typically in the C16-40 range, more typically in the C24 to C40 range, and having from 1 to 110 alkoxy groups. The alkoxy groups are selected from the group consisting of C2-C6 oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated fatty alcohols are preferred, and the ethoxylated alcohols and propoxylated alcohols are more preferred. The alkoxylated alcohols may be used alone or in mixtures with those alkoxylated materials disclosed herein-above.

Representative preferred examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10), steareth-10 (a stearyl alcohol ethoxylate having an average degree of ethoxylation of 10), steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and mixtures of the proceedings.

Commercially available corresponding nonionic surfactants are for example Brij® nonionic surfactants from Croda, Inc., Edison, N.J. Typically, Brij® is the condensation products of aliphatic alcohols with from 1 to 54 moles of ethylene oxide, the alkyl chain of the alcohol being typically a linear chain and having from 8 to 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. C8-C30 alcohols, with sugar or starch polymers. These compounds can be represented by the formula (S)n-O—R wherein S is a sugar moiety such as glucose, fructose, mannose, galactose, and the like; n is an integer of from 1 to 1000, and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a C8-C20 alkyl group, and n is an integer of from 1 to 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present disclosure are glyceryl esters and polyglyceryl esters, including but not limited to, glyceryl monoesters, typically glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of C16-C22 saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of C16-C22 fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Croda, Inc., Edison, N.J.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoistearate and sorbitan sesquioleate are particularly preferred emulsifiers for use in the present disclosure.

Also suitable for use as nonionic surfactants are alkoxylated derivatives of glyceryl esters, sorbitan esters, and alkyl polyglycosides, wherein the alkoxy groups is selected from the group consisting of C2-C6 oxides and their mixtures, with ethoxylated or propoxylated derivatives of these materials being typical. Nonlimiting examples of commercially available ethoxylated materials include ethoxylated sorbitan mono-, di- and/or tri-esters of C12 to C18 fatty acids with an average degree of ethoxylation of from 2 to 20, such as the products sold under the name TWEEN® by the company Uniqema).

Non-limiting examples of anionic surfactants include compounds in the classes known as alkyl sulfates, alkyl ether sulfates, alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates, isethionates and mixtures thereof. Specific examples of anionic surfactants include the ammonium, monoethanolamine, diethanolamine, triethanolamine, isopropylamine, sodium, potassium, lithium, or magnesium salts of lauryl sulfate, dodecylbenzene-sulfonate, lauryl sulfosuccinate, lauryl ether sulfate, lauryl ether carboxylate, lauryl sarcosinate, cocomethyl tauride, and sulfosuccinate half ester amide and mixtures thereof.

Non-limiting examples of amphoteric and zwitterionic surfactants include alkyl, alkyl dimethyl, alkylamido, alkyl amide, alkylamidopropyl, or alkyl dimethylammonium betaine; alky amidopropyl or alkyl sulfobetaine; alkyl, alkylampho, or alkylamphocarboxy glycinate; alkyl, or alkyl substituted imidazoline mono or dicarboxylate; sodium salts of alkyl mono- or dicarboxylates; alkyl beta amino acids; alkyl amidopropyl, or alkyl ether hydroxysultaine; alkyl amidopropyl dimethyl ammonia acetate; alkyl ampho mono- or diacetate; alkyl, or alkyl ampho, or alkyl imino dipropionate; alkyl amphopropionate; alkyl beta amino propionic acid; alkyl dipropionate; alkyl beta iminodipropionate; branched or n-alkyl dimethylamidopropionate; alkyl carboxylated propionate; alkyl, or methyl alkyl imidazoline; fluorinated alkyl amphoteric mixtures.

Specific examples include cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate and mixtures thereof.

The composition of the present disclosure contains at least one skin active agent. The at least one skin active agent includes photoprotective agents, self-tanning agents, desquamating agents, depigmenting agents, moisturizing agents, skin lightening agents, anti-aging ingredients, anti-wrinkle agents, anti-dandruff agents and mixtures thereof. Non-limiting examples of the at least one skin active agent include α-hydroxy acids, β-hydroxy acids, α-keto acids, β-keto acids, retinoids, anthralins, anthranoids, peroxides, lithium salts, antimetabolites, vitamin D, antioxidants, ingredients that could promote moisturization and desquamating agents.

As active agents that may be used in the composition of the present disclosure, examples that may be mentioned include moisturizers, for example, protein hydrolysates and polyols such as glycerol, glycols, for instance polyethylene glycols, and sugar derivatives; natural extracts; anti-inflammatory agents; procyannidol oligomers; vitamins, for instancevitamin A (retinol), vitamin C (ascorbic acid), vitamin E (tocopherol), vitamin B5 (panthenol), vitamin B3 (niacinamide), derivatives of these vitamins (especially esters) and mixtures thereof; urea; caffeine; depigmenting agents such as kojic acid, hydroquinone and caffeic acid; salicylic acid and its derivatives; α-hydroxy acids such as lactic acid and glycolic acid and derivatives thereof; retinoids such as carotenoids and vitamin A derivatives; sunscreens; self-tanning agents; hydrocortisone; melatonin; algal, fungal, plant, yeast or bacterial extracts; enzymes; DHEA and its derivatives and metabolites; antibacterial active agents, for instance 2,4,4'-trichloro-2'-hydroxydi-phenyl ether (or Triclosan), 3,4,4'-trichloro-carbanilide (or Triclocarban) and the acids indicated above and especially salicylic acid and its derivatives; mattifying agents and mixtures thereof.

Preferred embodiments of the compositions of the present disclosure include skin active agents chosen from hydroxy acids, vitamins, sunscreens, UV filters, humectants, glycols, polyols, self-tanning ingredients, antioxidants and mixtures thereof.

Other preferred embodiments of the compositions of the present disclosure include skin active agents chosen from photoprotective agents, self-tanning agents, desquamating agents, depigmenting agents, moisturizing agents, skin lightening agents, anti-aging ingredients, anti-wrinkle agents, anti-dandruff agents and mixtures thereof.

Non-limiting examples of sunscreens include benzophenones, bornelone, butyl PABA, cinnamidopropyl trimethyl ammonium chloride, disodium distryrylbiphenyl disulfonate, PABA, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, ethylhexyl dimethyl PABA, red petrolatum, and mixtures thereof.

Non-limiting examples of viscosity modifiers include water swellable/soluble cationic polymers from quaternized polysaccharides such as trimethyl ammonium substituted epoxide of hydroxyethyl cellulose, diallyldimethyl ammonium salts of hydroxyethylcellulose, deacylated chitin or chitosan, dihydroxypropyl chitosan trimonium chloride, hydroxypropltrimethyl ammonium chloride guar, locust bean, or konjac mannan gum; quaternized synthetics such as acrylamide dimethyl diallyl ammonium chloride copolymers, acrylamide/dimethyl diallyl ammonium chloride/acrylic acid terpolymer, quaternized poly(vinyl pyrrolidone/dimethyl amino ethylmethacrylate), poly(vinylpyrrolidone/methacrylamidopropyl trimethylammonium chloride), polyvinyl pyrrolidone/methylvinylimidazolinium chloride or methyl sulfate copolymer, chloroethylether/dimethylaminopropylamine/adipate or azelate terpolymer, vinylpyrrolidone/methacrylamidopropyl trimethylammonium chloride, acrylonitrile/acrylic acid/dimethylpropanediammonium acrylates sulfate terpolymer.

Further suitable viscosity modifiers include anionic or nonionic polysaccharide polymers such as gum tragacanth, sodium or propylene glycol alginate, kappa-, iota-, or lambda-carrageenan, guar or hydroxyl propyl guar gum, karaya gum, gum arabic, locust bean gum, konjac mannan gum, gellan, xanthan, succinoglycan or its acidic or enzymatic hydrolysates, sodium carboxymethyl cellulose, methycellulose, hydroxyethylcellulose, hydroxypropylmethylcellulose, and hydroxypropylcellulose; and/or hydrophobically modified anionic, cationic, or nonionic polymers such as, but not limited to, alkyl and/or substituted hydroxyethylcellulose, lauryl dimethyl ammonium substituted epoxide of hydroxyethylcellulose, propoxylated cellulosic, xanthan, succinoglycan, or polygalactomannoses, alkyl methacrylates/crosslinked acrylic acid copolymer and/or acrylonitrile/acrylates block copolymer.

Non-limiting examples of antibacterial agents include bacitracin, phenol, benzethonium chloride, erythromycin, neomycin, tetracycline, chlortetracycline and mixtures thereof.

Non-limiting examples of preservatives include polyvinyl alcohol, phenoxyethanol, benzyl alcohol, methyl paraben, propyl paraben and mixtures thereof.

Non-limiting examples of pH adjusting agents include potassium acetate, sodium carbonate, sodium hydroxide, phosphoric acid, succinic acid, sodium citrate, citric acid, boric acid, lactic acid, sodium hydrogen carbonate and mixtures thereof.

Bleaching agents include, but are not limited to, hydrogen peroxide, perborate and persulfate salts. EDTA and other aminocarboxylates may be used as sequestering agents. Anti-dandruff agents such as zinc pyrithione, salicylic acid, climbazole, ketoconazole, sulfur piroctone olamine, selenium sulfide and mixtures thereof may also be used as an auxiliary ingredient.

The at least one auxiliary ingredient is present in the composition in a preferred amount of from about 0.1 to about 50% by weight, more preferably from about 0.1 to about 30% by weight, and even more preferably from about 0.5 to about 20% by weight, based on the total weight of the composition.

The compositions described above are useful as compositions for treating keratinous substrates. These compositions include hair care products such as shampoos and conditioners, products for treating skin such as skin cleansers and personal hygiene products and products for cleaning and treating lips and nails. For example, when the keratinous substrate being treated is hair, the compositions of the present disclosure may impart shine and conditioning to the hair. The compositions of the present disclosure can also provide color retention properties to the artificial color in hair. In particular, the composition of the present disclosure may be provided in the form of a shampoo or rinse-out conditioner which preserves or inhibits the loss of artificial color (or enhances color retention) in hair when the hair is subjected to one or more washings or shampooings. In certain embodiments, the composition of the present disclosure can be applied to hair that has been previously treated with an artificial color. In other embodiments, an artificial color comprising a colorant, such as a dye compound, can be deposited onto the hair concurrently with the application of the composition of the present disclosure to form artificially colored hair. As used herein, the term "concurrently" (and variations thereof) refers to methods of treatment wherein the hair is colored in the same treatment session that includes treatment with the inventive compositions. Thus, the colorant may be included in the present composition or it can be applied separately, i.e., before, during or after application of the present composition provided that both applications are performed during the same treatment session.

Similar properties, along with styling, may be provided when the composition is in the form of a leave-on product.

The compositions of the present disclosure may also serve as a carrier vehicle for the auxiliary ingredients as described above.

When an auxiliary agent chosen from lipophilic compounds is present in the compositions of the present disclosure, such compositions were found to impart durable shine to hair, that is, when the hair contacted with such compositions was shampooed and rinsed with water, the hair remained shiny and healthy-looking.

In other preferred embodiments of the present disclosure, when an auxiliary agent chosen from cationic polymers is present in the compositions of the present disclosure, such compositions were found to inhibit or reduce frizz on hair.

When the keratinous substrate is skin, the compositions may impart protection from the sun (sunscreens) or provide skin benefits by serving as a carrier vehicle for skin actives (moisturizing agents, anti-acne agents, anti-wrinkle agents, anti-aging agents, depigmenting agents, whitening agents, etc.).

The method of treatment to be provided will depend on the keratinous substrate being targeted and, consequently, the specific ingredients contained in the composition used to effectuate the treatment. One of ordinary skill in the art will easily be able to determine these variables.

Having described the subject matter of the present disclosure by way of illustration and example for purposes of clarity of understanding, it will be apparent to one of ordinary skill in the art that the same can be performed by modifying or changing the subject matter within a variety of conditions, formulations and other parameters without affecting its scope or any specific embodiment thereof, and that such modifications or changes are intended to be encompassed within the scope of the appended claims.

EXAMPLES

The following examples are for illustrative purposes only and are not intended to limit the scope of the claims.

Example 1

Alkoxylated Monoamine

PEG-15 Cocamine (Efficiency Study)

Five swatches of International Hair Importers "IHIP" Platinum Bleached hair per treatment type (control and test) were dyed with a commercial hair dye. Initial L*A*B* color values were measured using Konica Minolta Spectrophotometer. Swatches were then shampooed with the following formulas:

| Control | |
|---|---|
| Sodium lauryl sulfoacetate | 5.0% |
| Disodium laureth sulfosuccinate | 5.0% |
| Cocamidopropyl Betaine | 1.75% |
| Octylacrylamide/acrylates/ butylaminoethylmethacrylate copolymer | 6.0% |
| Aminomethyl propanol | 1.28% |
| Capric/caprylic Triglyceride | 1.0% |
| DI Water | Q.S. to 100% |
| Test | |
| Sodium lauryl sulfoacetate | 5.0% |
| Disodium laureth sulfosuccinate | 5.0% |
| Cocamidopropyl Betaine | 1.75% |
| Octylacrylamide/acrylates/ butylaminoethylmethacrylate copolymer | 6.0% |
| PEG-15 Cocamine | 12.63% |
| Capric/caprylic Triglyceride | 1.0% |
| DI Water | Q.S. to 100% |

* Note that the percentage of the ingredients listed above are based on the total weight of each composition and that the ingredients are at 100% activity levels.

Shampoo weighing 0.4 g per gram of hair was applied onto the hair and massaged in for 15 seconds; the hair was then rinsed for 10 seconds (80 gph, 32° C.). The shampooing cycle was repeated for total of 5 times. The hair was dried completely and then measured for final L*A*B* values. The delta E value was then calculated and statistical analysis was performed.

The ΔE values for the Test and Control samples were 3.443 and 8.050, respectively. Since a lower ΔE value indicates less overall color change, the shampoo containing the disclosed composition had significantly less color change after 5 shampoos than the control (t-test).

Example 2

Alkoxylated Polyamine

Jeffamine T-403 (Polyoxypropylenetriamine)

(Efficiency Study)

Five swatches of IHIP Platinum Bleached hair per treatment type (control and test) were dyed with Redken Hi Fusion™ R. Initial L*A*B* color values were measured using Konica Minolta Spectrophotometer. Swatches were then shampooed with the following formulas:

| Control - Processed at 85° C. | |
|---|---|
| Sodium lauryl sulfoacetate | 5.0% |
| Disodium laureth sulfosuccinate | 5.0% |
| Cocamidopropyl Betaine | 1.75% |
| Octylacrylamide/acrylates/ butylaminoethylmethacrylate copolymer | 6.0% |
| Aminomethyl propanol | 1.28% |
| Capric/caprylic Triglyceride | 1.0% |
| DI Water | Q.S. to 100% |
| Test - Processed at room temperature. Deaerated overnight. | |
| Sodium lauryl sulfoacetate | 5.0% |
| Disodium laureth sulfosuccinate | 5.0% |
| Cocamidopropyl Betaine | 1.75% |
| Octylacrylamide/acrylates/ butylaminoethylmethacrylate copolymer | 6.0% |
| Polyoxypropylenetriamine | 2.29% |
| Capric/caprylic Triglyceride | 1.0% |
| DI Water | Q.S. to 100% |

* Note that the percentage of the ingredients listed above are based on the total weight of each composition and that the ingredients are at 100% activity levels.

Shampoo weighing 0.4 g per gram of hair was applied onto the hair and massaged in for 15 seconds; the hair was then rinsed for 10 seconds (80 gph, 32 C). The shampooing cycle was repeated for total of 5 times. The hair was dried completely and then measured for final L*A*B* values. The delta E was then calculated and statistical analysis was performed.

The ΔE values for the Test and Control samples were 4.944 and 8.050, respectively. Since a lower ΔE value indicates less overall color change, the shampoo containing the disclosed composition had significantly less color change after 5 shampoos than the control (t-test).

Example 3

Alkyl Monoamine

Stearamidopropyl Dimethylamine (Efficiency Study)

Four (4) swatches weighing five (5) grams each of IHIP Platinum Bleached hair per treatment type (control and test)

were prepared. Three (3) grams of product (see table below) per swatch were applied. The hair swatches were then baked in a 50° C. oven for 10 minutes.

| Control | |
|---|---|
| Ethanol | 92.62% |
| Octylacrylamide/acrylates/butylaminoethylmethacrylate copolymer | 6.0% |
| Aminomethyl propanol | 1.28% |
| Capric/caprylic Triglyceride | 33.7% |
| Basic Red # 51 | 0.1% |

| Test | |
|---|---|
| Ethanol | 54.9% |
| Octylacrylamide/acrylates/butylaminoethylmethacrylate copolymer | 6.0% |
| Stearamidopropyl Dimethylamine | 5.3% |
| Capric/caprylic Triglyceride | 33.7% |
| Basic Red # 51 | 0.1% |

* Note that the percentage of the ingredients listed above are based on the total weight of each composition and that the ingredients are at 100% activity levels.

Upon cooling at ambient temperature for 1 hour, the swatches were read for initial L*A*B* color values using the Konica Minolta Spectrophotometer. Shampoo weighing 0.4 g per gram of hair was applied onto the hair and massaged in for 15 seconds; the hair was then rinsed for 10 seconds (80 gph, 32 C). The shampooing cycle was repeated for a total of 3 cycles on the swatch and the data was recorded. Then the shampooing cycle was repeated an additional two cycles on the same sample, for a total of 5 cycles, and the data was recorded. The hair was dried completely and then measured for L*A*B* values at 3 and 5 shampoo cycles. The delta E value was then calculated and statistical analysis was performed.

The ΔE values for the Test and Control samples at 3 shampoo cycles were 16.577 and 23.261, respectively, and at 5 shampoo cycles were 20.831 and 30.368, respectively. Since a lower the ΔE value indicates less overall color change, the shampoo containing the disclosed composition had significantly less color change after 3 and 5 shampoos than the control (t-test).

Example 4

Alkyl Monoamine

Comparative Data of Durable Shine

Three swatches of IHIP Platinum Bleached hair (2 cm width, 19 cm length) per treatment type (control and test) were prepared. Initial shine values (Reich-Robbins) were measured using the SAMBA. The SAMBA is an instrument used to analyze the visual appearance of hair. It uses a polarization camera and obtains image of the hair, which is then analyzed to determine the shine and chroma of the hair tress. 0.4 g of the composition below per gram of hair was applied onto the hair, with even distribution.

| Test | |
|---|---|
| Ethanol | 55.0% |
| Octylacrylamide/acrylates/butylaminoethylmethacrylate copolymer | 1.0% |
| Aminopropyl phenyl trimethicone (and) phenylsilsesquioxane (and) phenyl trimethicone (and) trimethylethoxysilane | 2.0% |
| Capric/caprylic Triglyceride | 20.0% |
| DI Water | Q.S. to 100% |

| Comparative 1 | |
|---|---|
| Ethanol | 55.0% |
| Aminopropyl phenyl trimethicone (and) phenylsilsesquioxane (and) phenyl trimethicone (and) trimethylethoxysilane | 2.0% |
| Capric/caprylic Triglyceride | 20.0% |
| DI Water | Q.S. to 100% |

| Comparative 2 | |
|---|---|
| Ethanol | 55.0% |
| Aminopropyl phenyl trimethicone (and) phenylsilsesquioxane (and) phenyl trimethicone (and) trimethylethoxysilane | 2.0% |
| Octylacrylamide/acrylates/butylaminoethylmethacrylate copolymer | 1.0% |
| DI Water | Q.S. to 100% |

| Comparative 3 | |
|---|---|
| Ethanol | 55.0% |
| Octylacrylamide/acrylates/butylaminoethylmethacrylate copolymer | 1.0% |
| Capric/caprylic Triglyceride | 20.0% |
| DI Water | Q.S. to 100% |

| Comparative 4 | |
|---|---|
| Ethanol | 55.0% |
| Octylacrylamide/acrylates/butylaminoethylmethacrylate copolymer | 1.0% |
| DI Water | Q.S. to 100% |

| Comparative 5 | |
|---|---|
| Ethanol | 55.0% |
| Aminopropyl phenyl trimethicone (and) phenylsilsesquioxane (and) phenyl trimethicone (and) trimethylethoxysilane | 2.0% |
| DI Water | Q.S. to 100% |

| Comparative 6 | |
|---|---|
| Ethanol | 55.0% |
| Capric/caprylic Triglyceride | 20.0% |
| DI Water | Q.S. to 100% |

* Note that the percentage of the ingredients listed above are based on the total weight of each composition and that the ingredients are at 100% activity levels.

The swatches were measured for final shine in the same manner as the initial measurement. The swatches were then shampooed once (1× shampoo) with 10% sodium laureth sulfate shampoo using 0.4 g of shampoo per gram of hair. The hair was then washed for 15 seconds, followed by 10 seconds of rinsing. After drying the hair, the swatches were measured for final shine values. The percent change in shine was then calculated using the equation below:

% shine=$[(Ts)-(Tt)]/Rt \times 100$

Where:
Ts: Reich-Robbins shine value of treated hair swatches after 1× shampoo;
Tt: Initial Reich-Robbins shine value of treated hair swatches;
Rt: Initial Reich-Robbins shine value of untreated hair swatches.

Results of % change in shine are as below:

| | % change in shine |
|---|---|
| Test | −6.96 |
| Comparative 1 | −51.23 |
| Comparative 2 | 21.78 |
| Comparative 3 | −31.13 |
| Comparative 4 | 35.18 |
| Comparative 5 | −55.74 |
| Comparative 6 | −42.15 |

In the shine durability study above, the data represented is given in terms of the percent change in shine. A lower change in the percentage value indicates that the shine on the hair was more durable, while a large negative change in the percentage value indicates that the shine was not durable at all.

After the 1× shampoo, the % change Reich-Robbins shine value from the Test formula vs. Comparative 1 formula was −6.96 and −51.23, respectively. These values were statistically significant per t-test.

The % change Reich-Robbins shine value from the Test formula vs. Comparative 3 was −6.96 and −31.13 respectively. These values were statistically significant per t-test.

The % change Reich-Robbins shine value from the Test formula vs. Comparative 5 was −6.96 and −55.74 respectively. These values were statistically significant per t-test.

The % change Reich-Robbins shine value from the Test formula vs. Comparative 6 was −6.96 and −42.15 respectively. These values were statistically significant per t-test.

The results above show that the test formula provided more durable shine on the hair compared to comparative formulas 1, 3, 5 and 6.

On the other hand, a positive increase in the percent change in shine means that the initial treatment dulled the hair or caused the hair to be less shiny and the natural shine of the hair was regained once the hair was shampooed. Thus, given that the % change in Reich-Robbins shine value was positive for comparative example 2 and comparative example 4, these values cannot be utilized to evaluate the degree of durability of shine for these two examples because the treatment caused an initial dulling of the shine on the hair.

Example 5

Alkyl Monoamine

Anti-Frizz Evaluation

Four (4) swatches of frizzy wavy hair (1 cm width, 12 cm length) were prepared. Each swatch was shampooed once with the compositions illustrated below using 0.4 g of product per gram of hair. The product was evenly distributed onto hair, allowed to sit for one minute and rinsed for 10 seconds (80 gph, 32 C).

| Test | |
|---|---|
| VA/crotonates/vinyl neodecanoate copolymer | 1.0% |
| Stearamidopropyl dimethylamine | 0.4% |
| Polyquaternium-10 | 0.5% |
| Sodium Laureth Sulfate | 15.0% |
| Cocamidopropyl Betaine | 1.5% |
| Fragrance | 0.5% |
| DI Water | Q.S. to 100% |
| Control 1 | |
| VA/crotonates/vinyl neodecanoate copolymer | 1.0% |
| Stearamidopropyl dimethylamine | 0.4% |
| Sodium Laureth Sulfate | 15.0% |
| Cocamidopropyl Betaine | 1.5% |
| Fragrance | 0.5% |
| DI Water | Q.S. to 100% |
| Control 2 | |
| Polyquaternium-10 | 0.5% |
| Sodium Laureth Sulfate | 15.0% |
| Cocamidopropyl Betaine | 1.5% |

-continued

| | |
|---|---|
| Fragrance | 0.5% |
| DI Water | Q.S. to 100% |
| Control 3 | |
| DI Water | 100% |

*Note that the percentage of the ingredients listed above are based on the total weight of each composition and that the ingredients are at 100% activity levels.

Visual observations of the hair showed that the Test hair swatch had substantially less frizz and a better curl pattern than the Control hair swatches 1, 2 and 3. Additionally, the volume of the hair treated with the Test hair swatch was greatly reduced compared to the three Control hair swatches.

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or skill or knowledge of the relevant art. Accordingly, the description is not intended to limit the invention to the form disclosed herein. Also, it is intended that the appended claims be construed to include alternative embodiments.

What is claimed is:

1. A composition comprising:
   (a) at least one polymer derived from at least one of a sulfonic acid, carboxylic acid or phosphoric acid selected from the group consisting of Octylacrylamide/acrylates/butylaminoethyl methacrylate copolymer, VA/crotonates copolymer (and) isopropyl alcohol, Butyl ester of PVM/MA copolymer, Ethyl ester of PVM/MA copolymer, VA/crotonates/vinyl neodecanoate copolymer, VA/crotonates copolymer, Ethylene/acrylic acid copolymer, VA/vinyl butyl benzoate/crotonates copolymer, Acrylates/octylacrylamide copolymer, Acrylates/t-Butylacrylamide copolymer, VP/acrylates/lauryl methacrylate copolymer, Styrene/acrylates copolymer, Acrylates copolymer, Polyacrylate-3, Carbomer, Acrylates/C10-30 alkyl acrylate crosspolymer and mixtures thereof, wherein said at least one polymer is present in an amount of about 0.5% to about 8% by weight, based on the total weight of the composition;
   (b) at least one amino compound selected from the group consisting of alkyl monoamines and alkoxylated monoamines and mixtures thereof, wherein said at least one amino compound is present in an amount of from about 0.4% to about 15% by weight, based on the total weight of the composition; and
   (c) a cosmetically acceptable carrier; and
   (d) a lipophilic compound in an amount about 1% to about 50%, based on the total weight of the composition;
   wherein the alkyl monoamines of (b) are selected from the group consisting of:
   (b1) compounds corresponding to formula (IA):

$$RN(R')_2 \qquad (IA)$$

wherein
   R is a hydrocarbon radical containing at least 6 carbon atoms;
   R' is H or a hydrocarbon radical containing less than 6 carbon atoms;
   (b2) compounds corresponding to formula (IIA):

$$RCONHR'N(R'')_2 \qquad (IIA)$$

wherein:
R is a hydrocarbon radical containing at least 6 carbon atoms; R' is a divalent hydrocarbon radical containing less than 6 carbon atoms; and R" is H or a hydrocarbon radical containing less than 6 carbon atoms; and
(b3) aminosilicones having one amino group;
wherein the composition does not contain a non-ionic surfactant.

2. The composition of claim 1, wherein the alkyl monoamines are chosen from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamidopropyl dimethylamine, soyamidopropyl dimethylamine, wheat germamidopropyl dimethylamine, sunflower seedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, bras sicaamidopropyl dimethylamine, olivamidopropyl dimethylamine, palmitamidopropyl dimethylamine, stearamidoethyldiethylamine, aminopropyl phenyl trimethicone, and mixtures thereof.

3. The composition of claim 1, wherein the alkoxylated monoamines are chosen from:
compounds corresponding to formula (IC):

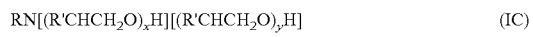
$$RN[(R'CHCH_2O)_xH][(R'CHCH_2O)_yH] \quad (IC)$$

wherein R is a hydrocarbon radical containing at least 6 carbon atoms;
x and y, independently of one another, represent numbers of from 0 to 100 provided that the sum of x+y is >0;
the groups R', which may be identical or different, represent hydrogen, or an alkyl group;
compounds corresponding to formula (IIC):

$$RNR''[(R'CHCH_2O)_xH] \quad (IIC)$$

wherein R is a hydrocarbon radical containing at least 6 carbon atoms;
x represents a number of from 1 to 100;
R' represents hydrogen, or an alkyl group; and
R" is a hydrogen or a hydrocarbon radical;
compounds corresponding to formula (IIIC):

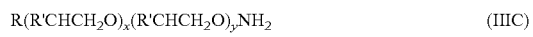
$$R(R'CHCH_2O)_x(R'CHCH_2O)_yNH_2 \quad (IIIC)$$

wherein R is a hydrocarbon radical containing at least 6 carbon atoms;
x and y, independently of one another, represent numbers of from 0 to 100 with the proviso that the sum of x+y is >0; and
the groups R', which may be identical or different, represent hydrogen, or an alkyl group.

4. The composition of claim 1, wherein the alkoxylated monoamines are chosen from PEG-2 Cocamine, PEG-3 Cocamine, PEG-5 Cocamine, PEG-10 Cocamine, PEG-15 Cocamine, PEG-20 Cocamine, PEG-2 Lauramine, PEG-12 Palmitamine, PEG-2 Rapeseedamine, PEG-2 Oleamine, PEG-5 Oleamine, PEG-6 Oleamine, PEG-10 Oleamine, PEG-15 Oleamine, PEG-20 Oleamine, PEG-25 Oleamine, PEG-30 Oleamine, PEG-3 Tallow Aminopropylamine, PEG-10 Tallow Aminopropylamine, PEG-15 Tallow Aminopropylamine, PEG-105 Behenyl Propylenediamine, aminosilicones having one amino group and at least one degree of alkoxylation, and mixtures thereof.

5. The composition of claim 1, wherein (b) is present in an amount ranging from about 0.5% to about 15% by weight, based on the total weight of the composition.

6. The composition of claim 1, wherein (c) comprises water, alone or in combination with at least one organic solvent.

7. The composition of claim 1, further comprising at least one auxiliary ingredient chosen from film forming agents, conditioning agents, cationic polymers, surfactants other than anionic surfactants, skin active agents, and mixtures thereof.

8. The composition of claim 1, wherein the lipophilic compound is chosen from plant oils, fatty esters, hydrocarbon oils, synthetic oils, fatty esters, silicones different from said polyacids, waxes, fatty acids having at least 12 carbon atoms and salts thereof, fatty alcohols, lipophilic vitamins and esters thereof, organic sunscreens, phospholipids, and mixtures thereof.

9. The composition of claim 7, wherein the cationic polymers are chosen from hexadimethrine chloride, polyquaternium-4, polyquaternium-6, polyquaternium-7, polyquaternium-10, polyquaternium-11, polyquaternium-16, polyquaternium-22, polyquaternium-32 and guar hydroxypropyltrimonium chloride.

10. The composition of claim 7, wherein the at least one auxiliary ingredient is present in an amount of from about 0.1% to about 50% by weight, based on the total weight of the composition.

11. The composition of claim 1, wherein the composition is free of monoethanolamine or diethanolamine or triethanolamine.

12. The composition of claim 1, wherein (a) comprises from about 0.5 to about 8% by weight of octylacrylamide/acrylates/butylaminoethyl methacrylate copolymer; and (b) comprises from about 0.4 to about 15% by weight of at least one amino compound chosen from PEG-15 Cocamine, stearamidopropyl dimethylamine, and aminopropyl phenyl trimethicone.

13. The composition of claim 1, further comprising a colorant.

14. A method of inhibiting artificial color loss from hair comprising:
(a) applying to hair a composition comprising:
(i) at least one polymer derived from at least one of a sulfonic acid, carboxylic acid or phosphoric acid selected from the group consisting of Octylacrylamide/acrylates/butylaminoethyl methacrylate copolymer, VA/crotonates copolymer (and) isopropyl alcohol, Butyl ester of PVM/MA copolymer, Ethyl ester of PVM/MA copolymer, VA/crotonates/vinyl neodecanoate copolymer, VA/crotonates copolymer, Ethylene/acrylic acid copolymer, VA/vinyl butyl benzoate/crotonates copolymer, Acrylates/octylacrylamide copolymer, Acrylates/t-Butylacrylamide copolymer, VP/acrylates/lauryl methacrylate copolymer, Styrene/acrylates copolymer, Acrylates copolymer, Polyacrylate-3, Carbomer, Acrylates/C10-30 alkyl acrylate crosspolymer and mixtures thereof, wherein said at least one polymer is present in an amount of about 0.5% to about 8% by weight, based on the total weight of the composition;
(ii) at least one amino compound selected from the group consisting of alkyl monoamines, alkoxylated monoamines and mixtures thereof, wherein said at least one amino compound is present in an amount of from about 0.4% to about 15% by weight, based on the total weight of the composition;
(iii) a cosmetically acceptable carrier; and (iv) a lipophilic compound in an amount of about 1% to about 50%, based on the total weight of the composition; and wherein the alkyl monoamines of (a)(ii) are chosen from:

(b1) compounds corresponding to formula (IA):

$$RN(R')_2 \qquad (IA)$$

wherein

R is a hydrocarbon radical containing at least 6 carbon atoms;

R' is H or a hydrocarbon radical containing less than 6 carbon atoms;

(b2) compounds corresponding to formula (IIA):

$$RCONHR'N(R'')_2 \qquad (IIA)$$

wherein:

R is a hydrocarbon radical containing at least 6 carbon atoms; R' is a divalent hydrocarbon radical containing less than 6 carbon atoms; and R'' is H or a hydrocarbon radical containing less than 6 carbon atoms; and (b3) aminosilicones having one amino group;

wherein the hair is previously artificially colored or an artificial colorant is applied to the hair concurrently with (a).

15. The method of claim 14, wherein the at least one amino compound is at least one alkyl monoamine chosen from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, bras sicaamidopropyl dimethylamine, olivamidopropyl dimethylamine, palmitamidopropyl dimethylamine, stearamidoethyldiethylamine, aminopropyl phenyl trimethicone, and mixtures thereof.

16. A method of imparting shine to hair comprising:
(a) applying to hair a composition comprising:
(i) at least one polymer derived from at least one of a sulfonic acid, carboxylic acid or phosphoric acid selected from the group consisting of Octylacrylamide/acrylates/butylaminoethyl methacrylate copolymer, VA/crotonates copolymer (and) isopropyl alcohol, Butyl ester of PVM/MA copolymer, Ethyl ester of PVM/MA copolymer, VA/crotonates/vinyl neodecanoate copolymer, VA/crotonates copolymer, Ethylene/acrylic acid copolymer, VA/vinyl butyl benzoate/crotonates copolymer, Acrylates/octylacrylamide copolymer, Acrylates/t-Butylacrylamide copolymer, VP/acrylates/lauryl methacrylate copolymer, Styrene/acrylates copolymer, Acrylates copolymer, Polyacrylate-3, Carbomer, Acrylates/C10-30 alkyl acrylate crosspolymer and mixtures thereof, wherein said at least one polymer is present in an amount of about 0.5% to about 8% by weight, based on the total weight of the composition;

(ii) at least one amino compound selected from the group consisting of alkyl monoamines alkoxylated monoamines and mixtures thereof, wherein said at least one amino compound is present in an amount of from about 0.4% to about 15% by weight, based on the total weight of the composition;

(iii) a cosmetically acceptable carrier; and (iv) a lipophilic compound in an amount of about 1% to about 50%, based on the total weight of the composition;

wherein the alkyl monoamines of (a)(ii) are chosen from:

(b1) compounds corresponding to formula (IA):

$$RN(R')_2 \qquad (IA)$$

wherein

R is a hydrocarbon radical containing at least 6 carbon atoms;

R' is H or a hydrocarbon radical containing less than 6 carbon atoms;

(b2) compounds corresponding to formula (IIA):

$$RCONHR'N(R'')_2 \qquad (IIA)$$

wherein:

R is a hydrocarbon radical containing at least 6 carbon atoms; R' is a divalent hydrocarbon radical containing less than 6 carbon atoms; and R'' is H or a hydrocarbon radical containing less than 6 carbon atoms; and (b3) aminosilicones having one amino group.

17. The method of claim 16, wherein the at least one amino compound is at least one alkyl monoamine chosen from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, bras sicaamidopropyl dimethylamine, olivamidopropyl dimethylamine, palmitamidopropyl dimethylamine, stearamidoethyldiethylamine, aminopropyl phenyl trimethicone, and mixtures thereof.

* * * * *

UNITED STATES PATENT AND TRADEMARK OFFICE
CERTIFICATE OF CORRECTION

PATENT NO. : 9,186,314 B2  
APPLICATION NO. : 13/762707  
DATED : November 17, 2015  
INVENTOR(S) : Nguyen et al.

Page 1 of 1

It is certified that error appears in the above-identified patent and that said Letters Patent is hereby corrected as shown below:

In the claims

Column 29, lines 17-18, claim 2, "sunflower seedamidopropyl" should read -- sunflowerseedamidopropyl --.

Column 29, line 23, claim 2, "bras sicaamidopropyl" should read -- brassicaamidopropyl --.

Column 31, line 39, claim 15, "bras sicaamidopropyl" should read -- brassicaamidopropyl --.

Column 32, line 51, claim 17, "bras sicaamidopropyl" should read -- brassicaamidopropyl --.

Signed and Sealed this
Nineteenth Day of April, 2016

Michelle K. Lee
*Director of the United States Patent and Trademark Office*